United States Patent [19]
Farris

[11] Patent Number: 5,102,398
[45] Date of Patent: Apr. 7, 1992

[54] PLUNGERLESS SYRINGE

[76] Inventor: Barry L. Farris, P.O. Box 1087, Pollock Pines, Calif. 95726

[21] Appl. No: 584,808

[22] Filed: Sep. 18, 1990

[51] Int. Cl.$^5$ ............................................ A61M 5/178
[52] U.S. Cl. ................................... 604/212; 222/94
[58] Field of Search .............. 604/212, 213, 214, 216, 604/217; 222/94, 96

[56] References Cited

U.S. PATENT DOCUMENTS

| | | | |
|---|---|---|---|
| 1,762,430 | 6/1930 | Tokita | 604/212 |
| 2,744,528 | 5/1956 | Barrett et al. | 604/212 |
| 2,768,623 | 10/1956 | Marchand . | |
| 2,911,972 | 11/1959 | Elinger . | |
| 3,089,489 | 5/1963 | Dunmire | 604/212 |
| 3,335,914 | 8/1967 | Strazdins et al. | 604/212 |
| 3,340,869 | 9/1967 | Bane . | |
| 3,557,788 | 1/1971 | Swartz . | |
| 3,712,295 | 1/1973 | Kline . | |
| 3,736,933 | 6/1973 | Szabo | 604/212 |
| 4,018,222 | 4/1977 | McAleer et al. . | |
| 4,130,117 | 12/1978 | Van Eck . | |
| 4,168,032 | 9/1979 | Sneider . | |
| 4,282,986 | 8/1981 | af Ekenstam et al. . | |
| 4,411,656 | 10/1983 | Cornett, III . | |
| 4,548,601 | 10/1985 | Lary . | |
| 4,753,638 | 6/1988 | Peters . | |

FOREIGN PATENT DOCUMENTS

| | | | |
|---|---|---|---|
| 0470700 | 9/1914 | France | 604/212 |
| 0557400 | 11/1943 | United Kingdom | 604/212 |

*Primary Examiner*—C. Fred Rosenbaum
*Assistant Examiner*—Sharon Finkel
*Attorney, Agent, or Firm*—Bernhard Kreten

[57] ABSTRACT

A hollow, molded, disposable, plastic syringe is provided with an air trap chamber in fluid communication with a collapsible container portion. With the air trap chamber extending upwardly from the container portion, air is trapped in the chamber when the container is collapsed to eject liquid out of the container.

14 Claims, 2 Drawing Sheets

PLUNGERLESS SYRINGE

FIELD OF THE INVENTION

This invention relates to medical devices and more particularly to a plungerless syringe having means for preventing air from being injected into a patient or infusion device.

BACKGROUND OF THE INVENTION

Every day large numbers of syringes are utilized in dispensing fluids. Still the primary device utilized for these injectors is a small cylindrical container or tube, and a plunger piston manually moved within the tube to eject liquid through an outlet at one end of the tube that is connected to a cannula or tubular needle. Some of such syringes are reutilized with proper sterilization in between uses.

A variation of the foregoing, which is in widespread use, is to position a sealed cartridge into a syringe-like holder, and a piston rod or actuator carried by the holder depresses a piston in the cartridge to eject fluid out of a needle attached to the cartridge. The tube and the needle are conveniently disposable; however, it is somewhat cumbersome to remove the cartridges and there is a risk of the operator being stuck with the needle during the removal process.

Considerable efforts have been expended to improve the foregoing apparatus by the use of disposable, plungerless syringes. A search for plungerless syringes has uncovered the following U.S. Pat. No. 2,768,623-Marchand; U.S. Pat. No. 2,911,972-Elinger; U.S. Pat. No. 3,340,869-Bane; U.S. Pat. No. 3,557,788-Swartz; U.S. Pat. No. 3,712,295-Kline; U.S. Pat. No. 4,018,222-McAleer et al.; U.S. Pat. No. 4,130,117-Van Eck; U.S. Pat. No. 4,168,032-Sneider; U.S. Pat. No. 4,282,986-af Ekenstam et al.; U.S. Pat. No. 4,411,656-Cornett, III; U.S. Pat. No. 4,548,601-Lary; and U.S. Pat. No. 4,753,638-Peters.

In general, these patents disclose a variety of small, plastic containers or ampoules which can be squeezed to eject the container contents through an outlet adapted to be connected to a needle to be inserted into a patient. Although these devices have been available for some time, they do not seem to be widely used. One reason for this may be that such plungerless syringes are deemed to present a possible safety hazard to the patient because of the possibility of air or gas being injected into the patient.

During any process of filling a plungerless syringe with liquid, there is inevitably some air or other gas which remains trapped in the container. Likewise there is usually gas within a plunger-type syringe. With a syringe having a plunger, the common technique of removing the gas before injecting liquid into the container is to point the needle of the syringe upwardly causing the gas to rise to the upper end adjacent the outlet. The syringe piston is then depressed sufficiently to force the air out of the syringe. The piston will remain in its partially depressed position so that it is easy for the operator to proceed with injecting the liquid into the patient or infusion device without concern for air being injected.

This procedure cannot be used satisfactorily with the plungerless syringe. While a plungerless syringe can also be oriented with the needle extending upwardly causing the trapped air to rise upwardly, it is very difficult to then carefully move the syringe to a horizontal position and to insert the needle into the patient while holding the plungerless syringe in a partially collapsed position. If the container is squeezed an additional amount during these steps, liquid is, of course, ejected and thus wasted. More importantly, the quantity of fluid being injected into the patient may be unknown and inaccurate. If the collapsing force on the container is relaxed, the container can return to its uncollapsed state, thus drawing contaminated ambient air back into the container through the needle. While the quantity of air initially in a plungerless container is relatively small, and would probably not cause danger to the patient, there is nevertheless a risk involved and hence it is desirable that the air injection risk be eliminated.

The Bane patent, referred to above, discloses a collapsible, bellows-like ampoule wherein, before the needle is inserted, one section of the bellows is collapsed to expel air. Presumably, this is done holding the needle upwardly. A button-like plug holds the section collapsed. While this approach would seem to be effective to remove air, the device is not seen in the market. Possibly the construction may be somewhat expensive.

The above-referenced Lary patent discloses an air vent in a double-walled syringe type container, and refers to ejecting air between a portion of the containers rather than from within the container containing liquid. It does however, prevent air intake into the inner container.

Thus a need exists for an inexpensive syringe that is practically disposable and that eliminates the air injection problem in an improved manner.

SUMMARY OF THE INVENTION

The present invention satisfies the above-expressed need by providing an inexpensive, blow-molded, collapsible container having a separate chamber which is in communication with the container that traps the air in the container. The chamber is positioned on one side of the container in a location that is generally perpendicular to the direction that the container is squeezed to collapse it. By positioning the syringe with the chamber extending upwardly, the liquid in the chamber will flow by gravity into the container displacing any air in the container into the chamber. Thus with the air trapped in the chamber, the syringe is maintained in a position with the chamber extending upwardly during the process of injecting liquid into the patient or infusion device. The chamber is located such that when the collapsing force is applied to the container, liquid is not forced into the chamber to displace the air.

The container is provided with an outlet portion that is conveniently attached to a needle. The needle can be attached to the container during its manufacturing process, however, it is preferable that the liquid outlet for the container be sealed by a suitable plug which is removed and replaced by the needle when the syringe is to be utilized. In accordance with another aspect of the invention, the outlet is closed by a plastic fiber formed integrally with the syringe and being attached to the syringe in a manner such that it can easily be removed by a manual pulling or twisting force applied to a tab attached to the fiber. Thus when the syringe is to be used, it is a simple matter to break the fiber and install a needle on the outlet of the syringe.

DETAILED DESCRIPTION OF THE PREFERRED EMBODIMENT

Figure 1:
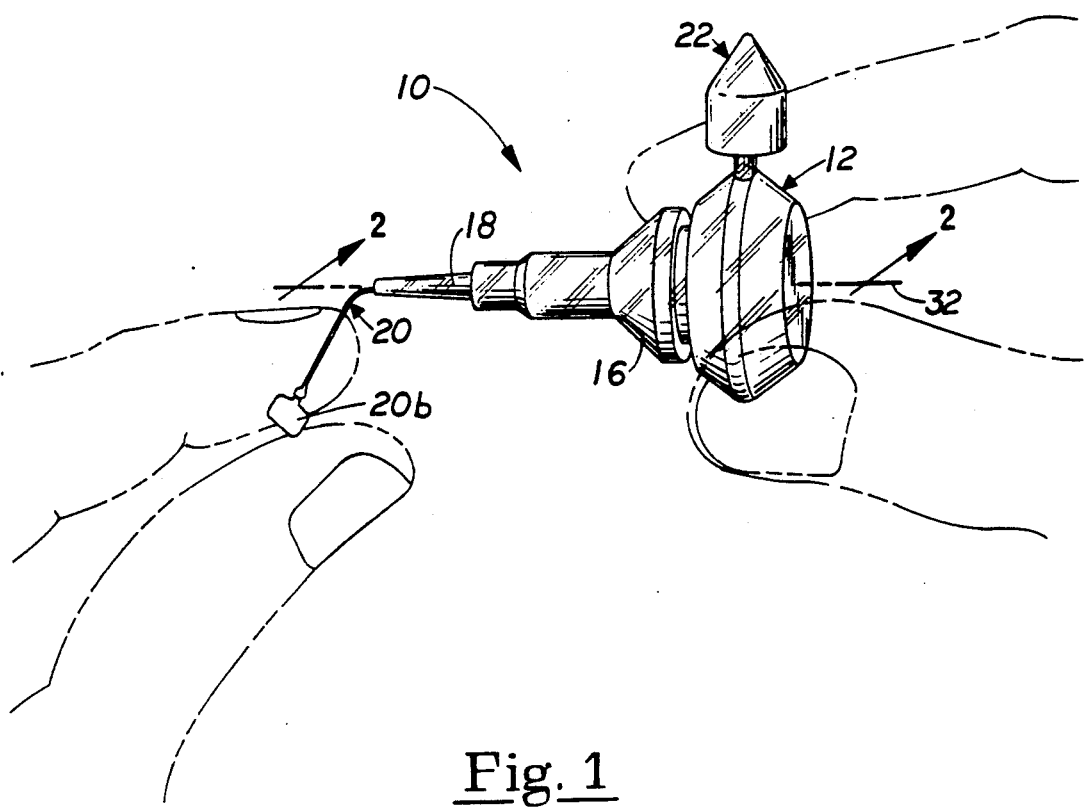
FIG. 1 is a perspective view showing the exterior of the syringe of the invention, with the user's fingers shown in phantom lines.
Figure 2:
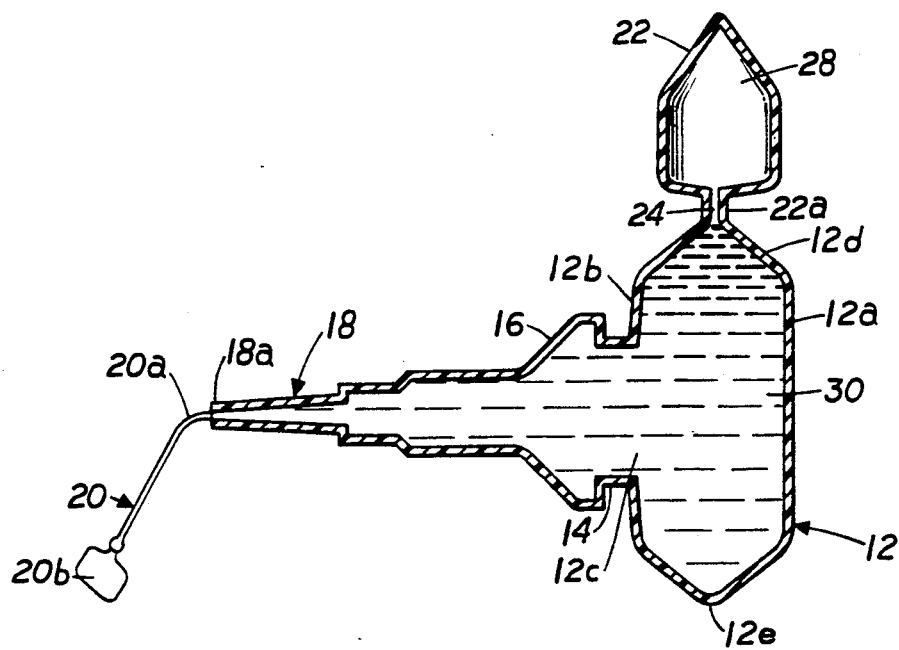
FIG. 2 is a cross-sectional view of the syringe of FIG. 1.
Figure 4:
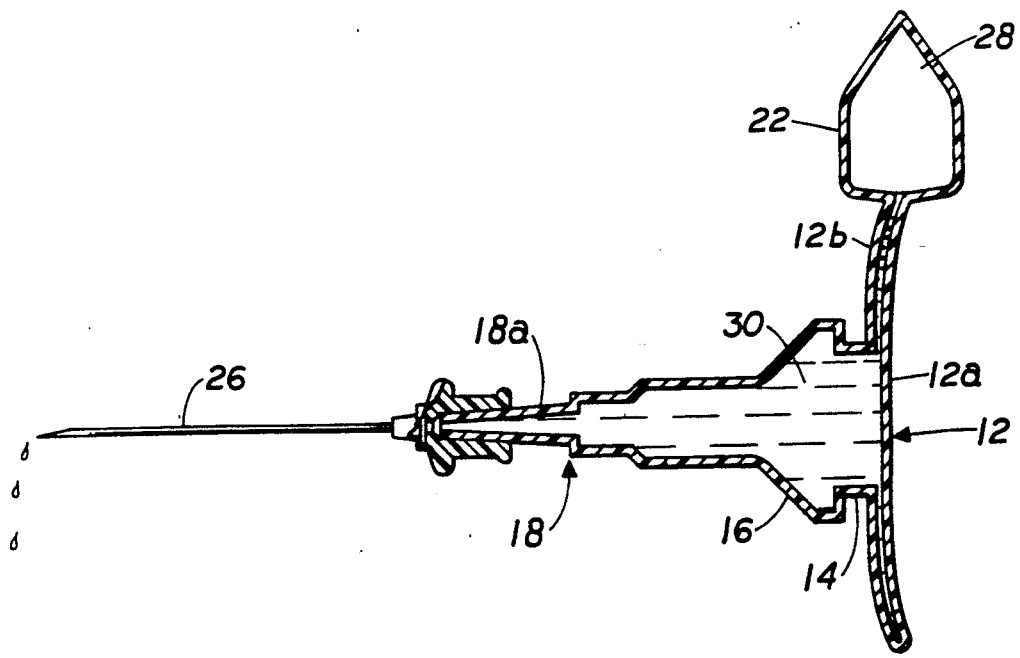
FIG. 4 is a cross-sectional view similar to FIG. 3 but with the container collapsed.

Referring to FIGS. 1 and 2, there is illustrated a plungerless syringe 10 in the form of a thin wall, hollow plastic body having a rear main portion forming a container 12, a neck 14 leading to a forward, finger-gripping portion 16, and an outlet portion 18, closed by a closure 20, and further including an air trap chamber 22 in fluid communication with the container 12. As seen, the container 12 has a bulbous disk shape, somewhat like one section or compartment of a bellows structure. The container includes a generally flat rear wall 12a, a generally flat forward wall 12b having a central opening 12c, and a main annular peripheral wall 12d having front and rear portions which taper radially outwardly to a generally cylindrical band 12e. The entire syringe 10 is blow-molded of suitable plastic, and the container portion 12 is sufficiently flexible such that the rear wall 12a may be depressed forwardly into engagement with the forward wall 12b to eject the contents of the container, as shown in FIG. 4.

The finger engaging portion 16 has a frusto-conical shape and is joined to the forward wall 12b of the container by a neck 14. The tubular outlet portion 18 is joined to the finger engaging portion 16 and includes a tip 18a having a tapered exterior to facilitate the mounting of a cannula or tubular needle thereon.

The closure 20 includes a flexible fiber formed integrally with the tip 18a and closing the outlet in the tip. The connection between the fiber 20a and the tip is such that the fiber can be broken away from the tip relatively easily to open the end of the tip. The opposite end of the fiber 20a has a flattened finger gripping portion 20b also made during the single molding operation.

The air trap chamber 22 has a generally cylindrical shape with a conical upper surface convenient for fabrication by blow molding. The chamber is in fluid communication with the container 12 by means of a short tubular connection 22a forming a passage 24. The connection is located at the container cylindrical band 12e, the widest portion of the container and at the approximate center of the container. The connection 22a is generally perpendicular or radial to the container axis 32, seen in FIG. 1.

As mentioned, the entire syringe is formed in a single molding operation and thus it is very inexpensive to fabricate. Consistent with blow molding, the wall thicknesses are relatively uniform throughout. The plastic employed is flexible but yet sufficiently stiff to retain its shape. While the container is sufficiently large such that its walls are easily collapsed, the smaller diameter component, such as the finger engaging portion 16 are stiffer, which is convenient for handling the unit.

During the fabrication process of the syringe, the liquid to be dispensed from the syringe is injected into the syringe either during the final step of the blow molding operation or as a separate step. Regardless of the approach used, there is always some air or other gas trapped within the syringe. As indicated above, it is a goal of the invention to prevent the injection of air into the patient or infusion device.

Figure 3:
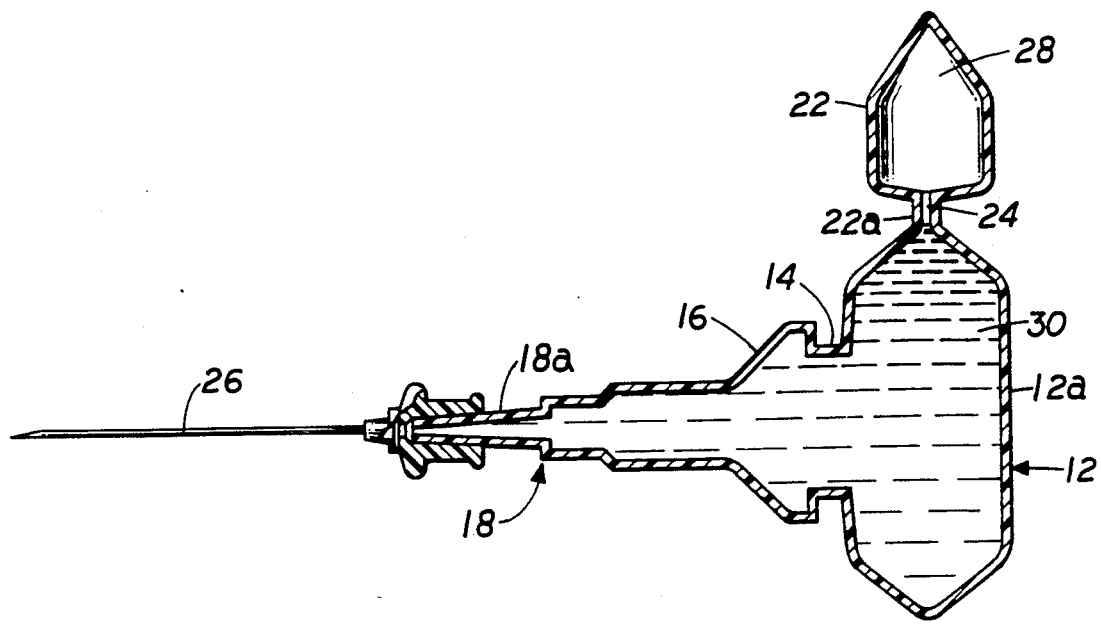
FIG. 3 is a cross-sectional view of the syringe of FIG. 2 with the outlet closure removed and replaced by a needle.

In use, the syringe is gripped by one hand, preferably on the finger engaging portion 16 while the tab 20b of the closure 20 is gripped with the fingers of the other hand, as suggested in FIG. 1. With a pulling and twisting force or movement, the fiber 20a of the closure 20 can be easily broken away from the tip of the outlet portion 18. A standard hypodermic needle or cannula 26 may then be positioned onto the tip 18a as shown in FIG. 3. Of course, the needle may be initially provided with a protective sheath (not shown) which is removed when the needle is to be used. As a further alternative, the needle together with its protective sheath may be mounted on the syringe outlet portion at the fabrication facility, and thus eliminating the need for the closure 20.

With the needle installed on the syringe and the unit ready to be used, the syringe is horizontally oriented with the passage 22a and the air trap 22 extending upwardly as shown in FIG. 3. This orientation causes any air 28 trapped in the syringe to move upwardly into the air trap 22 having been displaced by liquid 30 flowing by gravity out of the air trap. While maintaining this orientation, the needle is inserted into the patient, with two of the user's fingers engaging the finger engaging or gripping portion 16 while the user's thumb engages the rear wall 12a of the container. Pressing the wall 12a forwardly against the front wall 12b, ejects the liquid, as illustrated in FIG. 4. Because of the location of the air trap, the liquid ejecting force, along the axis of the syringe, does not eject the air into the patient. Probably some liquid will be forced into the air trap chamber, but the air trapped in that chamber will not be displaced by the liquid.

From the foregoing, it will be recognized that the air trap can be positioned in various locations and can have various shapes. However, it is important that it be located and connected to the container in a fashion such that the increased pressure during the liquid ejection steps does not force the air out of the chamber but instead causes the air to be trapped within the chamber 22.

The syringe can of course be made in whatever size desired. In one form of the invention, scheduled for production, the syringe container 12 has a volume of 3 milliliters and the air chamber has a volume of about 1 milliliter. The volume of liquid placed in that syringe must exceed 3 milliliters to allow for liquid in the forward portion which is not ejected.

What is claimed is:

1. A plungerless syringe comprising a hollow, collapsible container made of material which is sufficiently stiff to maintain its shape, but is sufficiently flexible to be manually collapsed by fingers of a user, said container having an outlet through which liquid in said container is ejected upon collapsing said container; and a gas trap in the form of a small chamber which is in fluid communication with said container, said chamber being physically connected to said container by a passage such that when said container and said chamber are oriented so that gas in said container is displaced into said chamber, the gas will be trapped in said chamber prior to and when said container is collapsed to eject the liquid.

2. The syringe of claim 1 wherein said container includes a rear wall, and a front wall with said outlet therein, said rear wall adapted to be compressed towards said outlet, and said chamber communicates with said container with a passage which is offset from said front and rear walls.

3. The syringe of claim 1, wherein said container includes a rear wall adapted to be depressed towards said outlet to force the liquid out of said container, and said container and said chamber are connected by a passage located peripherally from said rear wall so that depressing said rear wall towards said outlet does not cause the gas to be displaced out of said chamber and into said container.

4. The syringe of claim 1, wherein said container has an annular peripheral wall interposed between a rear wall and a front wall, said peripheral wall connected to said chamber by a passage.

5. The syringe of claim 1, including a fiber-like closure initially blocking said outlet, said closure being formed integral with structure forming said outlet but being readily, manually broken away from said structure when the liquid in said container is dispensed.

6. The syringe of claim 1, wherein said container and said chamber are simultaneously formed as a single unit in solitary molding operation.

7. The syringe of claim 1 wherein said container has a bellows disk shape somewhat like one section of a bellows including a forward wall with said outlet therein, a rear wall and an annular peripheral wall, and wherein said chamber is connected by a passage opening to said peripheral wall, said container being collapsible by pressing said rear wall towards said forward wall.

8. A plungerless disposable syringe comprising:
a thin-wall plastic container which is sufficiently stiff to maintain its shape, but is sufficiently flexible to be manually collapsed by fingers of a user;
liquid in said syringe together with a small quantity of gas;
said container having an outlet through which the liquid can be ejected by collapsing said container; and
a chamber connected to said container by a small passage, said passage and said chamber being located such that when said syringe is oriented in its normal fashion to eject liquid out of said outlet by collapsing said container, and with said chamber extending upwardly, the gas will be trapped in said chamber as the liquid is ejected.

9. A plungerless syringe comprising a hollow, collapsible container made of material which is sufficiently stiff to maintain its shape, but is sufficiently flexible to be manually collapsed by fingers of a user, said container having an outlet through which liquid in said container is ejected upon collapsing said container; and
an air trap in the form of a small chamber which is in fluid communication with said container, said chamber being physically connected to said container in a manner and location such that when said container and said chamber are oriented so that air or other gas in said container is displaced upwardly into said chamber, the air or other gas will be trapped in said chamber when said container is collapsed to eject the liquid,
wherein said container has a bellows disk shape somewhat like one section of a bellows including a forward wall with said outlet therein, a rear wall and an annular peripheral wall, and wherein said chamber is connected by a passage opening to said peripheral wall, said container being collapsible by pressing said rear wall towards said forward wall.

10. A dispenser for ejecting liquid housed within said dispenser while retaining gas residing within said dispenser, comprising, in combination:
a container having a liquid outlet and a gas outlet, said liquid outlet spaced from said gas outlet,
said gas outlet communicating with a chamber to store the gas therewithin,
said container formed with at least one wall which moves from a first position to a second position,
said first position defining a liquid retaining position whereupon the liquid remains stored within said container,
and said second position defining a liquid ejected position whereupon the liquid has been expelled from said dispenser and said one wall occludes said gas outlet from said liquid outlet by collapsing said container and covering said gas outlet.

11. A syringe type liquid dispenser, comprising, in combination:
a container having an outlet for the egress of liquid therefrom,
ejecting means on said container which forces the liquid from said container,
a gas trap chamber in communication with an interior of said container to receive any gas which may be entrained in the liquid prior to ejecting the liquid from the container,
and said gas trap chamber including a passageway spaced from said outlet and allowing fluid communication between said chamber and said container to segregate the gas in the chamber from the liquid in the container.

12. The syringe of claim 11 including said ejecting means includes means for closing said passageway while ejecting the liquid from the outlet 13. A method of injecting liquid from a plungerless syringe which includes a collapsible container having an outlet through which liquid is ejected while the container is being collapsed, said method comprising the steps of:
orienting said container so that a gas trap chamber which has a passage which is in fluid communication with said container extends generally upwardly so that any gas in said container will be displaced into said chamber; and
maintaining said chamber in its upward position while collapsing said container in a manner such that liquid is ejected out of said container through said outlet and the gas remains trapped in said chamber during said container collapsing step.

14. The method of claim 13, wherein said orienting step includes orienting an outlet of said chamber in a generally horizontal direction with the chamber extending upwardly.

* * * * *